US00PP23706P2

(12) United States Plant Patent
Nielsen

(10) Patent No.: US PP23,706 P2
(45) Date of Patent: Jul. 2, 2013

(54) *DAHLIA* PLANT NAMED 'DATYVE'

(50) Latin Name: *Dahlia Cav.*
Varietal Denomination: DATYVE

(75) Inventor: Rune Harboe Nielsen, Grönnegyden (DK)

(73) Assignee: Dalina Genetics APS, Odense N (DK)

( * ) Notice: Subject to any disclaimer, the term of this patent is extended or adjusted under 35 U.S.C. 154(b) by 0 days.

(21) Appl. No.: 13/374,956

(22) Filed: Jan. 25, 2012

(51) Int. Cl.
*A01H 5/00* (2006.01)

(52) U.S. Cl.
USPC ..... Plt./321

(58) Field of Classification Search
USPC ..... Plt./321
See application file for complete search history.

(56) References Cited

PUBLICATIONS

Application information from Community Plant Variety Office (CPVO) website for corresponding CPVO application No. 2011/1743 filed Jul. 8, 2011 (1 page) (http://www.cpvoextranet.cpvo.europa.eu).
Application information for Canadian Plant Breeders' Rights application No. 11-7382 filed Oct. 6, 2011, published in Plant Varieties Journal No. 82, Jan. 2012 (1 page) (www.inspection.gc.ca/plants/plant-breeders-rights/plant-varieties-journal).

*Primary Examiner* — Annette Para
(74) *Attorney, Agent, or Firm* — Foley & Lardner LLP

(57) ABSTRACT

A new distinct cultivar of *Dahlia* plant named 'DATYVE', characterized by its upright to slightly spreading shape, with stiff and strong lateral stems and thick compound leaves, with up to 12 leaflets. The color of the mature leaves are RHS Green 139A (upper side) and RHS Grayed-green 191A (Underside). Compound leaves are 6-24 cm in length, and 8-18 cm in width. Hardly no single leaves are present. Composite flower heads are 9-10 cm in diameter, with a large number of ray florets (about 120 to 150). The ray florets are RHS Orange-red N30B and RHS Yellow 2A near base.

6 Drawing Sheets

Latin name of the genus and species of the claimed plant: *Dahlia Cav.*
Variety denomination: 'DATYVE'.

BACKGROUND OF THE INVENTION

The present invention relates to a new and distinct cultivar of *Dahlia* plant, botanically known as *Dahlia Cav.*, of the Compositae (Asteraceae) family, hereinafter referred to by the cultivar name 'DATYVE'.

The new *Dahlia* cultivar is a product of a planned breeding program conducted by the inventor, Rune Nielsen, in Stige, Denmark. The objective of the breeding program is to develop a new *Dahlia* cultivar with an upright, strong and healthy growth habit, suitable for large scale container production and with good garden performance; fully double flowers creating globular-shaped flower head (composite flower heads with many ray florets) with an attractive inflorescence color.

The new *Dahlia* cultivar originated from a cross, made in a controlled breeding program by the inventor in 2008, in Stige, Denmark. The female or seed parent is Yellow-orange *Dahlia* cultivar designated 'DASYTTEN' (Patented, U.S. Plant Pat. No. 21,037). The male or pollen parent is unknown.

Asexual reproduction of the new *Dahlia* cultivar by terminal cuttings was first performed in September, 2009 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DATYVE', which in combination distinguish this *Dahlia* as a new and distinct cultivar:

1. Cultivar with upright to slightly spreading shape;
2. Cultivar with stiff and strong lateral stems and thick compound leaves, with up to 12 leaflets. Color of mature leaves RHS 139A (upper side) RHS 191A (Underside);
3. Compound leaves with 3 to 12 leaflets, 6-24 cm in length, and 8-18 cm in width and hardly any single leaves present.
4. Composite flower heads, with a large number of ray florets (about 120 to 150); and
5. Ray florets which are RHS Orange-red N30B and RHS Yellow 2A near base.

Plants of the new *Dahlia* 'DATYVE' differ from plants of the parent, 'DASYTTEN' (Patented, U.S. Plant Pat. No. 21,037) in the traits described in Table 1. (The male parent is unknown).

TABLE 1

| | Comparison with Parent Variety | |
|---|---|---|
| Trait | New Cultivar 'DATYVE' | Comparison Cultivar 'DASYTTEN' |
| Plant Size | | |
| Height: | About 30-45 cm. | About 45-50 cm. |
| Diameter: | About 40-50 cm. | About 35-40 cm. |
| Overall Plant Shape: | Upright to spreading with basal branching. Inflorescences in composite heads. | Cylindrical, upright to outward, with basal branching. Inflorescences in composite heads. |
| Basal branches with flowers | | |
| Length: | 25-35 cm. | 25-40 cm. |
| Diameter: | 12-14 mm | 6-11 mm |

TABLE 1-continued

| Comparison with Parent Variety | | |
|---|---|---|
| Trait | New Cultivar 'DATYVE' | Comparison Cultivar 'DASYTTEN' |
| Strength: | Stiff and strong. | Stiff and strong. |
| Color: | RHS Brown 200B at the oldest parts. RHS Yellow-green 146B on most parts. | RHS Brown 200A on older stems, and RHS Yellow-green 147B, on Younger stems or stems exposed to less light. |
| Leaves | | |
| Colour mature upper side: | RHS Green 139A. | RHS Grayed-green N 189A. |
| Underside: | RHS Grayed-green 191A. | RHS Grayed-green 191B. |
| Peduncle | | |
| Colour mature: | RHS Brown 200B | RHS Brown 200B |
| Colour immature: | RHS Yellow-green 146B | RHS 146B |
| Color of ray florets Upper side: | RHS Orange-red N30B and RHS Yellow 2A near base. | Near base RHS 1B, transitioning to RHS 17C at apex. |

Of the many commercial cultivars known to the present inventor, the most similar in comparison to the new *Dahlia* 'DATYVE' is the *Dahlia* cultivar 'DASYTTEN', in the characteristics described in Table 2: Table 2—Comparison with Comparison Variety

TABLE 2

| Comparison with Comparison Variety | | |
|---|---|---|
| Trait | New Cultivar 'DATYVE' | Comparison Cultivar 'DASYTTEN' |
| Plant Size | | |
| Height: | About 30-45 cm. | About 45-50 cm. |
| Diameter: | About 40-50 cm. | About 35-40 cm. |
| Overall Plant Shape: | Upright to spreading with basal branching. Inflorescences in composite heads. | Cylindrical, upright to outward, with basal branching. Inflorescences in composite heads. |
| Basal branches with flowers | | |
| Length: | 25-35 cm. | 25-40 cm. |
| Diameter: | 12-14 mm | 6-11 mm |
| Strength: | Stiff and strong. | Stiff and strong. |
| Color: | RHS Brown 200B at the oldest parts. RHS Yellow-green 146B on most parts. | RHS Brown 200A on older stems, and RHS Yellow-green 147B, on Younger stems or stems exposed to less light. |
| Leaves | | |
| Colour mature upper side: | RHS Green 139A. | RHS Grayed-green N189A. |
| Underside: | RHS Grayed-green 191A. | RHS Grayed-green 191B. |
| Peduncle | | |
| Colour mature: | RHS Brown 200B | RHS Brown 200B |
| Colour immature: | RHS Yellow-green 146B | RHS 146B |
| Color of ray florets Upper side: | RHS Orange-red N30B and RHS Yellow 2A near base. | Near base RHS 1B, transitioning to RHS 17C at apex. |

BRIEF DESCRIPTION OF THE PHOTOGRAPHS

The accompanying photographs illustrate the overall appearance of the new *Dahlia* 'DATYVE' showing the colors as true as is reasonably possible with colored reproductions of this type. Colors in the photographs may differ slightly from the color value cited in the detailed botanical description, which accurately describe the color of 'DATYVE'.

DETAILED BOTANICAL DESCRIPTION

Figure 1:
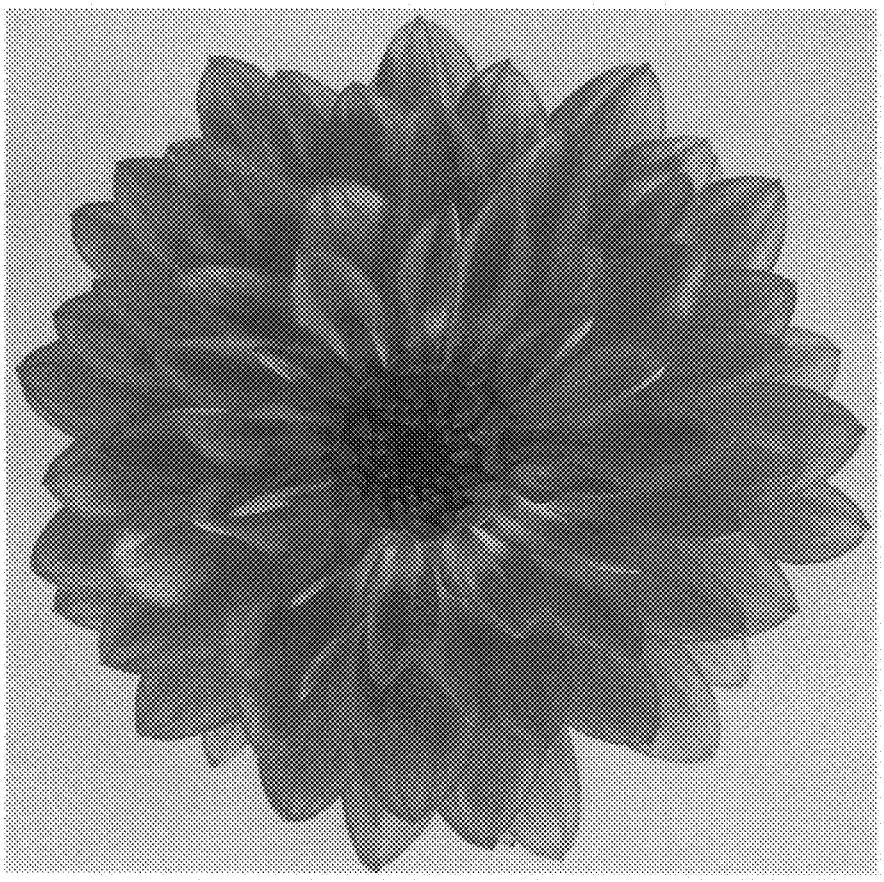
FIG. 1 shows a close-up view of the composite flower head from 'DATYVE'.
Figure 2:
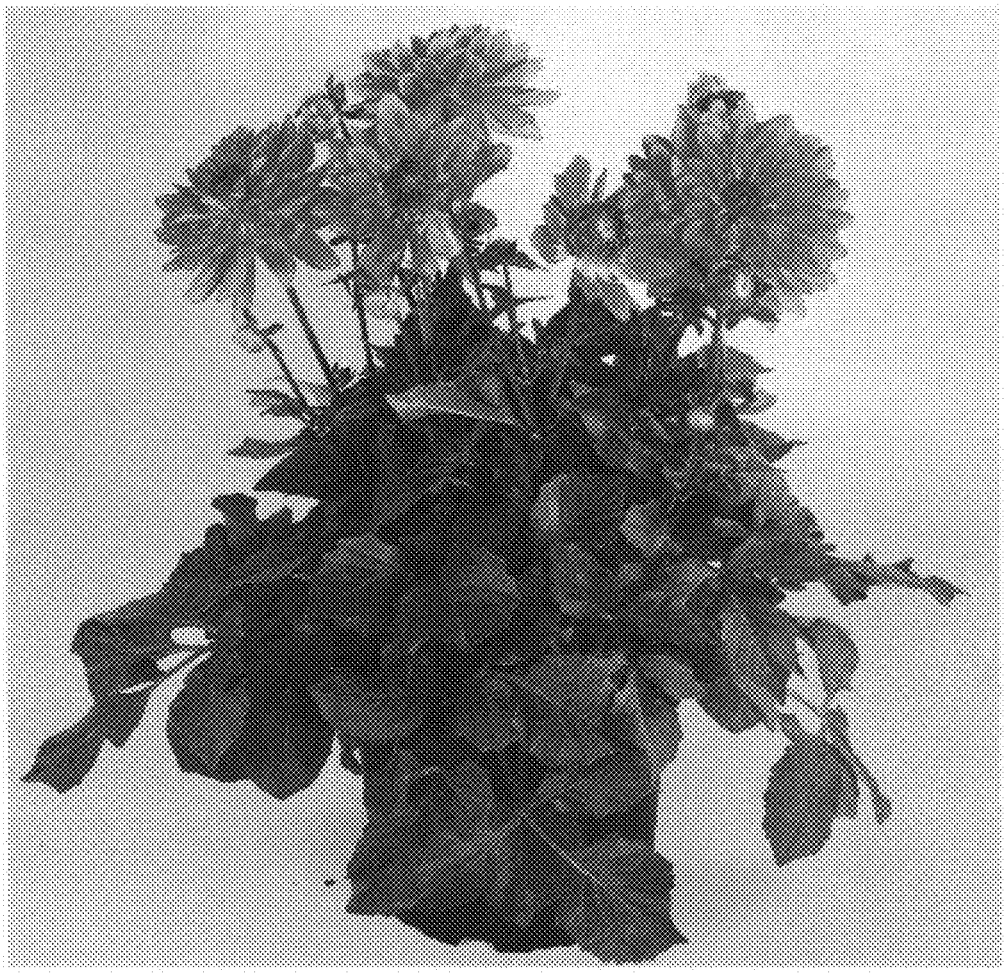
FIG. 2 shows a side view perspective of a typical flowering plant of 'DATYVE' in a 19 cm pot, at 8 weeks of age after potting the young plant.
Figure 3:
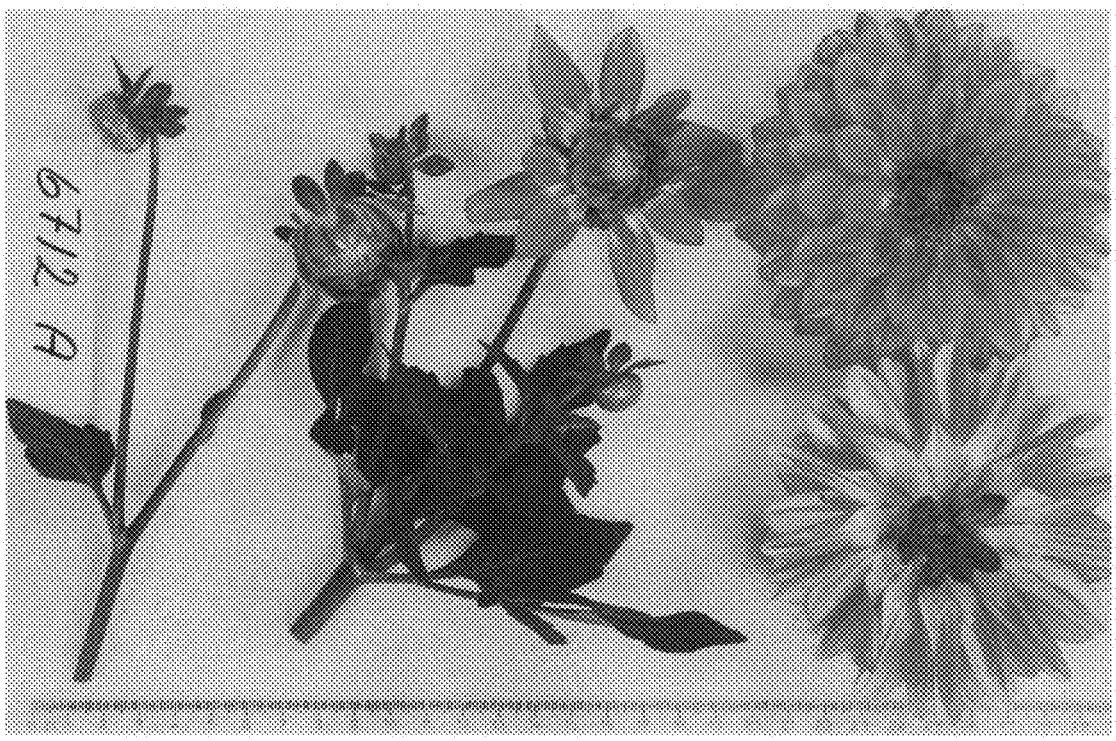
FIG. 3 shows a close-up view of different development stages of the composite flower head of 'DATYVE'.
Figure 4:
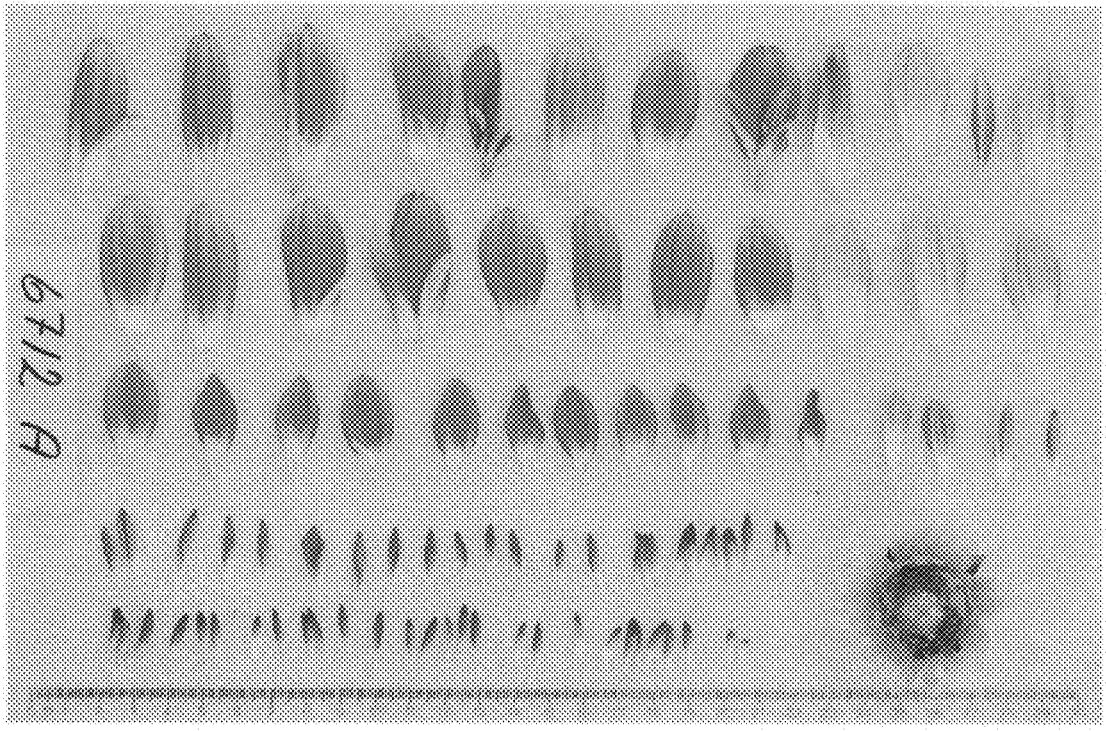
FIG. 4 shows a close-up view of the 120-150 ray florets from one composite flower head of 'DATYVE'
Figure 5:
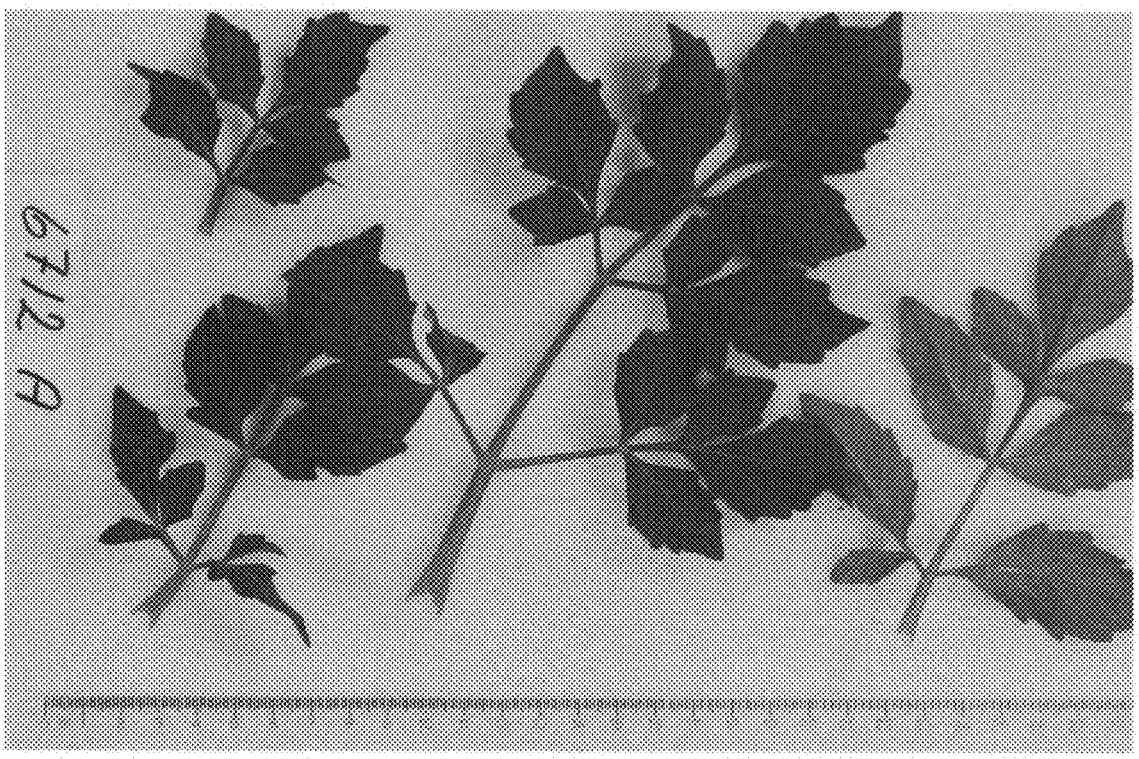
FIG. 5 shows a close-up view of the different compound leaf sizes of 'DATYVE'.
Figure 6:
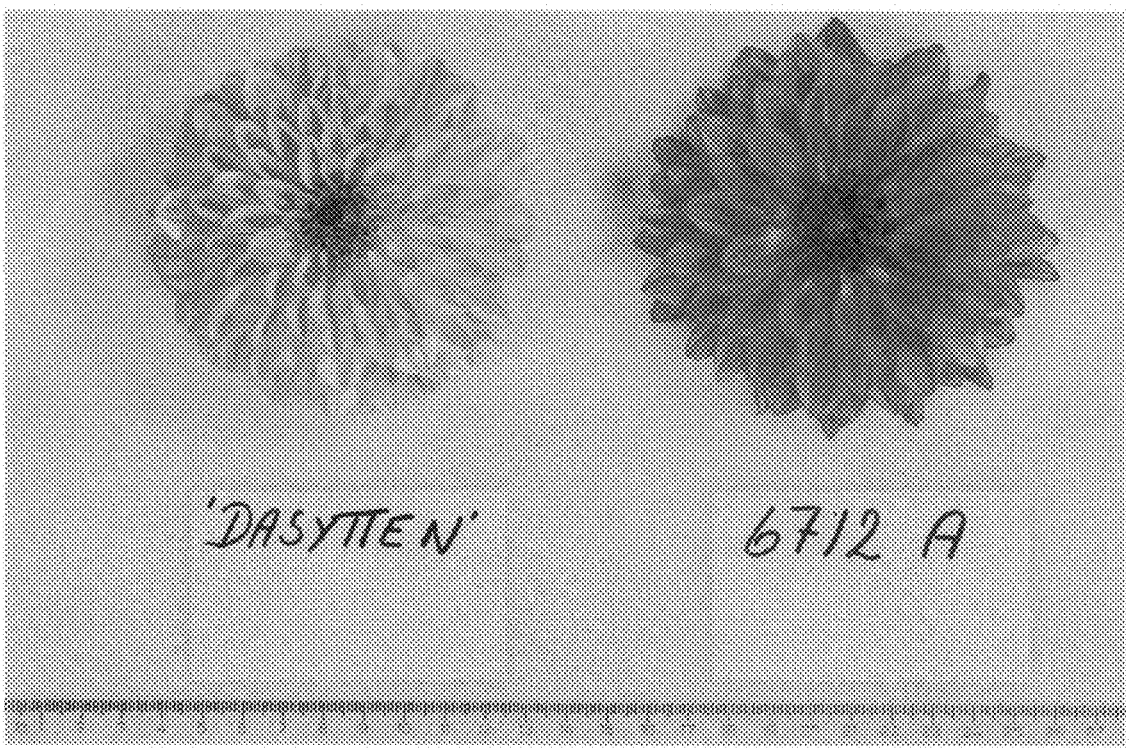
FIG. 6 shows a comparison between 'DASYTTEN' and 'DATYVE' (Breeders reference: 6712A).

The new *Dahlia* 'DATYVE' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dahlia* 'DATYVE' as grown in a protected environment in a glass, greenhouse in Fyn, Odense, Denmark, under conditions which closely approximate those generally used in commercial practice. During propagation, conducted in a glasshouse, vegetative cuttings were planted 6 Jul. 2011 in small propagation pots with peat as substrate, and then placed in a plastic tunnel averaging about 21° C. and received photoperiodic treatments of 18 hours. Supplementary light was given when natural light fell below 3000-4000 Lux. Rooting occurred about 12 days after planting. In third week after planting the cutting (27 Jul. 2011), young plants were potted in an 19 cm pot in a glass covered greenhouse, maintained at 18° C. to 26° C. during the day, and at 17° C. to 19° C. during the night. Plants were grown under natural daylight conditions. Irrigation was done with water. The EC measured in the soil was maintained between 2.0 to 3.0. One week after potting, the first growth regulation was given: a spray with 85% daminozide, 0.2%, 40-100 ml/m2. During the production time, 9 additional sprayings were given with 85% daminozide, 0.2%, 40-100 ml/m2.

Color references are made to The Royal Horticultural Society Colour Chart (R.H.S.), 2001 edition, except where general colors of ordinary significance are used. Color values were taken under September daylight conditions at approximately 12:00 PM and 2:00 PM in Fyn, Odense, Denmark. The age of the 'DATYVE' plants described is 10-11 weeks (including propagation time).

Classification:

*Botanical.—Dahlia Cav.*

Parentage:

*Female or seed parent.—Dahlia* variety designated DASYTTEN (Patented, U.S. Plant Pat. No. 21,037).

*Male or pollen parent.*—Unknown.

Propagation:

*Type*.—Vegetative terminate cuttings.

*Time and temperature to initiate roots*.—About 9 to 12 days at 21° C. in tunnels or flat covered in a greenhouse.

*Time and temperature to produce a rooted young plant*.—About 21 days at 21° C. during rooting phase, followed by 18° C.

*Rooting habit*.—Fine, fibrous; Color of root: RHS Yellow-white 158C.

*Tuber development*.—Plants might develop tubers in late fall when planted outside.

Plant description:

*General appearance and form*.—Upright to slightly spreading shape. Inflorescences in composite heads.

*Growth rate*.—Growing about 3 to 6 cm per week during production period.

*Plant height* (*from soil level to top of plant plane*).—About 30-45 cm.

*Plant width* (*spread*).—About 40-45 cm.

*Crop time to produce a mature flowering plant*.—It requires 3 to 4 weeks to produce a young plant in a 35 mm propagation plug. After potting 7 to 11 weeks are required to produce finished flowering plants in 19 cm pots.

Stem:

*Shape*.—Round.

*Length* (*pinched above* 3 *pair of leaves*).—About 5-6 cm.

*Diameter*.—About 12-16 mm.

*Strength*.—Stiff and strong.

*Aspect*.—Upright.

*Texture*.—Fluted woody surface.

*Color*.—RHS Brown 200B, with stripes of RHS Gray-brown 199C.

Branches:

*Branching habit*.—Basal branching with lateral branches.

*Number of basal branches per plant*.—About 3-5 (when pinched above 3 pair of leaves).

*Length* (*including flowers*).—About 25-35 cm.

*Diameter*.—About 12-14 mm.

*Strength*.—Stiff and strong.

*Aspect*.—Upright to slightly spreading.

*Texture*.—Glabrous and slightly furrowed, Mammillate near the base.

*Color*.—Mature: RHS Brown 200B at the oldest parts. RHS Yellow-green 146B on most parts.

*Internodes length*.—About 15-50 mm.

*Internodes color*.—RHS Yellow-green 146B.

Foliage description:

*Type*.—Compound leaves divided into 3-12 leaves.

*Number of leaves per branch*.—About 8-12 per branch.

*Color of leaves* (*leaves and leaflets*).—Color of upper side (mature) RHS 139A. Color of underside (mature) RHS 191A. Color of upper side (immature) RHS 137A. Color of underside (immature) RHS 137C.

*Venation* (*leaves and leaflets*).—Pattern: Pinnate. Color of upper side: RHS 146A. Color of underside: RHS 146C.

Compound leaves:

*Number of leaflets per compound leaf*.—3-12.

*Length of compound leaf*.—6-24 cm.

*Width of compound leaf*.—8-18 cm.

*Petiole of compound leaves*.—Shape: Semi circular, with deep furrow on adaxial side. Length: 3-6 cm. Diameter: 3-10 mm. Texture: Smooth and glabrous. Color: RHS Yellow-green 146B to RHS Brown 200B on sun exposed areas.

*Leaflets of compound leaf*.—Terminal leaflet quantity: 1. Terminal leaflet length: 5-10 cm. Terminal leaflet width: 4-9 cm. Terminal leaflet shape: Ovate. Terminal leaflet shape at apex: Acuminate. Terminal leaflet shape at base: Cordate to rounded (not always symmetric). Terminal leaflet margin: Dentate. Terminal leaflet texture (both sides): Rugose. Rachis length: 1-4 cm. Rachis diameter: 2-4 mm. Rachis color: RHS Yellow-green 146B. Lateral leaflet quantity: 2-4. Lateral leaflet length: 3-8 cm. Lateral leaflet width: 3-6 cm. Lateral leaflet overall shape: Ovate. Lateral leaflet shape at apex: Acuminate (mostly asymmetric). Lateral leaflet shape at base: Rounded (not always symmetric). Lateral leaflet margin: Dentate. Lateral leaflet texture (both sides): Rugose.

Simple leaves: Hardly ever present.

Inflorescence description:

*Natural flowering season*.—Grown outside as a bedding plant, flowering occurs continuously during growing season from spring to autumn/(In Denmark, from June to beginning of October). Plants can be brought to flower anytime when grown under the recommended greenhouse conditions.

*Time to flower*.—50 to 80 days from potting a young plant until flowering.

*Inflorescence longevity on the plant*.—Inflorescence will maintain good color and substance for about 6-10 days; however, the longevity of individual inflorescence is highly dependent on temperature and light conditions. Inflorescence persistent.

*Type*.—Composite flower heads.

*Arrangement and shape*.—Persistent, single, composite inflorescences from leaf axils. Disc and ray florets arranged acropetally in a composite flower head. Upright, slightly spreading. Terminal young flower head/buds initially 0-30°. Buds from axillary shoots 90-120°. When flower opens 30-90°.

*Quantity of inflorescences heads*.—Freely flowering; about 14 buds and open inflorescences per plant.

*Fragrance*.—None.

*Bud* (*Inflorescences head*).—Rate of opening (from showing color to fully open): 4 to 10 days. The rate of opening is highly dependent on temperature and light conditions. Length: About 10-14 mm. Diameter: About 18-22 mm. Shape: Flat globular. Texture: Glabrous, shining. Color: RHS Yellow-green 144C.

*Peduncle*.—From both terminate and axillary shoots. Length: About 8-14 cm. Diameter: About 4-6 mm. Angle: About 0-20° from vertical. Strength: Stiff and strong. Texture: Glabrous. Color (mature/immature, directly sun exposed): RHS Brown 200B. Color (mature/immature not directly sun exposed): RHS Yellow-green 146B. sun exposed):

*Inflorescence head*.—Depth (height): 3-5 cm. Diameter: 9-10 cm.

*Ray florets*.—Arrangement: Imbricate, in about 9 to 12 whorls of ray florets, each with 9 to 11 florets to equal a total of about 120-150 ray florets per flower head, depending on light and temperature conditions.

Quantity per Inflorescence head: 120-150. Length: 45-50 mm. Widths: 20-25 mm. Overall shape: Obovate. Apex shape: Obtuse. Base shape: Acuminate, slightly fused. Margin: Entire. Texture: Glabrous (upper side and underside). Colour when opening fused ray floret starting to show color: RHS Orange N34B. Colour when fully opened Color upper side: RHS Orange-red N30B and RHS Yellow 2A near base. Color underside: RHS RHS Orange-red 34B. Nerves and the area near base are RHS Yellow 2A.

*Disc florets*.—Arrangement: 30-40 yellow-orange disc florets arranged in center of inflorescence head. Apperance: Quantity per Inflorescence head: 30-40. Length: 8-12 mm. Diameter: 2 mm. Overall shape: Tubular. Apex shape: Star with 5 triangular tips. Base shape: Fused to tube. Color RHS Yellow-orange 21A.

*Phyllary*.—Arrangement: One subtending each floret. Quantity: 160-200. Length: 12-22 mm. Width: 6-9 mm. Overall shape: Rounded. Shape at apex: Acute with rounded tip. Shape at base: Fused. Margin: Entire. Color: Mature: RHS Yellow-green 151C. RHS Yellow-green 146A on underside of the 8-10 phyllaries in the outer whorl, Immature: RHS Yellow-green 151C.

*Bracts*.—Arrangement and appearance: Reflexed, involucral bracts. Quantity: 7-8. Length: 12-18 mm. Width: 6-8 mm. Overall shape: Subulate. Apex shape: Acute. Base shape: Sessile. Margin: Entire. Texture: Glabrous. Colour mature Upper side: RHS 137A. Underside: RHS 137B. Colour immature Upper side: RHS 137A. Underside: RHS 137B.

Reproductive organs:

*Androecium*.—Location: Disc florets only. Stamen number: 5, fused into synandrous tube around style. Stamen length: About 6-8 mm. Anther shape: Tubular. Anther length: About 4-5 mm. Pollen amount: Some. Pollen color: RHS N25C.

*Gynoecium*.—Location: Ray and disc florets. Quantity: 1. Pistil length: 12-14 mm. Stigma shape: Bifurcate. Stigma length: About 4 mm. Stigma color: Not visible due to the cover of pollen brushed of the anthers. It then appears RHS N25C. Style length: About 6 mm. Style color: RHS 151C. Ovary color: RHS 151C.

Seed/fruit: Seed and fruit production has not been observed.

Disease/pest resistance: Resistance to pathogens and pests common to *Dahlia* has not been observed.

Disease/pest susceptibility: Susceptibility to pathogens and pests common to *Dahlia* has not been observed.

Temperature tolerance: Plants of the new *Dahlia* have exhibited good tolerance rain, wind and drought; however, flowering may cease during hot periods (temperatures above 25° C.). Low temperature tolerance to 1° C.

Growth regulators: Daminozide (85% water soluble dryconcentrate formulation).

What is claimed is:

1. A new and distinct cultivar of *Dahlia* plant named 'DATYVE', as illustrated and described herein.

* * * * *